(12) United States Patent
Berndt

(10) Patent No.: US 7,244,252 B2
(45) Date of Patent: Jul. 17, 2007

(54) MEDICAL DEVICE WITH VISUAL INDICATOR AND RELATED METHODS OF USE

(75) Inventor: Malka Berndt, Lexington, MA (US)

(73) Assignee: Scimed Life Systems, Inc., Maple Grove, MN (US)

( * ) Notice: Subject to any disclaimer, the term of this patent is extended or adjusted under 35 U.S.C. 154(b) by 182 days.

(21) Appl. No.: 10/720,190

(22) Filed: Nov. 25, 2003

(65) Prior Publication Data
US 2005/0113808 A1 May 26, 2005

(51) Int. Cl.
*A81B 17/00* (2006.01)
(52) U.S. Cl. .......................................................... 606/1
(58) Field of Classification Search ................ 606/100, 606/1, 205
See application file for complete search history.

(56) References Cited

U.S. PATENT DOCUMENTS

| | | | |
|---|---|---|---|
| 4,382,063 A * | 5/1983 | Romito et al. ................. 422/57 |
| 5,359,993 A * | 11/1994 | Slater et al. ................. 600/133 |
| 5,384,264 A * | 1/1995 | Chen et al. ................... 436/525 |
| 5,518,927 A * | 5/1996 | Malchesky et al. ............. 436/1 |
| 5,602,040 A * | 2/1997 | May et al. .................... 436/514 |
| 5,657,764 A * | 8/1997 | Coulter et al. ............... 600/591 |
| 5,662,712 A * | 9/1997 | Pathak et al. ............. 623/23.64 |
| 5,739,041 A * | 4/1998 | Nazareth et al. ............. 436/518 |
| 5,786,220 A * | 7/1998 | Pronovost et al. .......... 436/518 |
| 5,900,379 A * | 5/1999 | Noda et al. .................. 436/518 |
| 6,140,136 A * | 10/2000 | Lee ............................. 436/518 |
| 6,174,309 B1 * | 1/2001 | Wrublewski et al. ......... 606/45 |
| 6,218,189 B1 * | 4/2001 | Antonoplos et al. ........... 436/1 |
| 6,786,897 B2 * | 9/2004 | Mc Ie et al. ..................... 606/1 |
| 2002/0110931 A1 * | 8/2002 | Quattrocchi et al. ........ 436/518 |
| 2003/0036747 A1 * | 2/2003 | Ie et al. .......................... 606/1 |
| 2003/0216724 A1 * | 11/2003 | Jahns .......................... 606/41 |
| 2003/0216732 A1 * | 11/2003 | Truckai et al. ................ 606/49 |
| 2003/0216733 A1 * | 11/2003 | McClurken et al. .......... 606/51 |
| 2003/0220637 A1 * | 11/2003 | Truckai et al. ................ 606/28 |
| 2004/0049172 A1 * | 3/2004 | Root et al. ...................... 606/1 |
| 2004/0186469 A1 * | 9/2004 | Woloszko et al. ............. 606/41 |
| 2004/0253142 A1 * | 12/2004 | Brewster et al. .............. 422/58 |
| 2004/0265778 A1 * | 12/2004 | Kliff et al. .................. 433/143 |

OTHER PUBLICATIONS

International Search Report and Written Opinion in PCT/US2004/037914, dated Feb. 11, 2005.
Copy of a chart of inks from http://www.tempil.com/Sterilizationlinks.html on or before Jul. 30, 2003.

* cited by examiner

*Primary Examiner*—Michael Peffley
*Assistant Examiner*—Alex Toy
(74) *Attorney, Agent, or Firm*—Finnegan, Henderson, Farabow, Garrett & Dunner LLP

(57) ABSTRACT

Embodiments of the invention relate to a medical device with a visual indicator that changes color when exposed to a particular environment and/or chemical. The visual indicator may be printed or otherwise affixed on a portion of a medical device, for example the handle, and initially have the same color as that portion. When exposed to a particular environment and/or chemical, the visual indicator changes color so that it has a different color than that portion of the medical device.

47 Claims, 4 Drawing Sheets

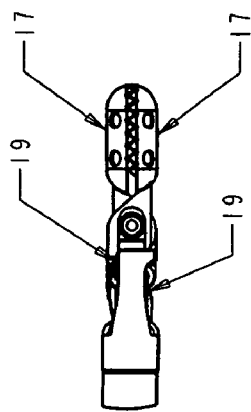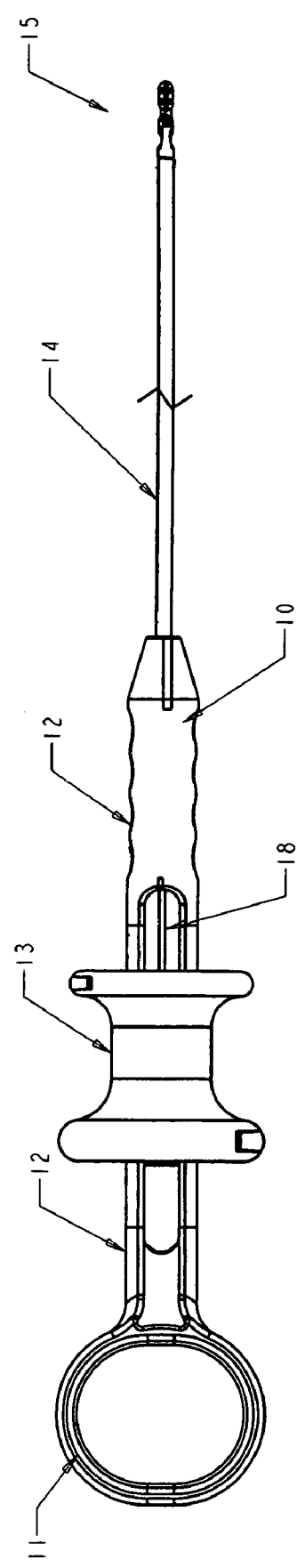

MEDICAL DEVICE WITH VISUAL INDICATOR AND RELATED METHODS OF USE

FIELD OF THE INVENTION

Embodiments of the invention relate to a medical device with a visual indicator that changes color when exposed to a particular environment and/or chemical. The visual indicator may be printed or otherwise affixed on a portion of a medical device, for example the handle, and initially have the same color as that portion. When exposed to a particular environment and/or chemical, the visual indicator changes color so that it has a different color than that portion of the medical device.

BACKGROUND OF THE INVENTION

Prior to using a medical device, the device should be sterile and not exposed to hazardous environments and/or chemicals. Medical devices are used with and inside the human body, and the use of unsterile medical devices can cause infections or even death. In addition, and for at least these reasons, many medical devices are designed as single use devices and should not be reused on a second patient. As it is sometimes difficult to tell by just visual inspection, however, whether a particular medical device is sterile, has been exposed to potentially hazardous environments and/or chemicals, or already used, an indicator of prior use or an unsterile state is desired.

One way to determine that a medical device is sterile is if it is used immediately after removing it from its original, unopened, sealed packaging. However, as there may be a time delay between when the medical device is removed from that packaging and when it is used by the user, and the actual user may differ from the person who removed the medical device from the packaging, this method may be of limited use.

Another way to determine that a medical device is sterile is through the placement of labels, stickers, or tapes on the medical device or packaging. The labels, stickers, or tapes may contain chemicals that change color, for example, when exposed to a nonsterile or other undesirable environment, an undesirable temperature, or a potentially hazardous chemical for any duration. However, labels, stickers, or tapes placed on the device packaging presents the same problems discussed above. In addition, labels, stickers, or tapes can be removed and/or fall off when placed on the medical device itself.

Accordingly, another method of determining the sterility of a medical device is desired.

SUMMARY OF THE INVENTION

In accordance with the invention, an embodiment of the invention includes a device to perform a medical procedure including a medical device and an indicator produced directly on the medical device, the indicator capable of undergoing a color change when exposed to a particular environment.

In another embodiment, the invention includes a medical device including a handle, a distal end effector, an elongate portion connecting the handle to the distal end effector, and a visual indicator produced directly on a surface of the handle. The indicator is configured to be substantially the same color as the surface of the handle before being exposed to a particular environment. The indicator is also configured to be a different color than the surface of the handle after being exposed to the particular environment.

In various embodiments, the invention may include one, some, or all of the following features. The medical device may include a handle, a distal end effector, and an elongate portion connecting the handle to the distal end effector. The indicator may be produced directly on the handle. The handle may include a ring portion and an elongate portion. The indicator may be produced directly on the ring portion. The indicator may be printed directly on the medical device. The indicator may be configured to show a symbol when it undergoes the color change. The particular environment may include a chemical. The chemical may be one of EtO gas and formaldehyde gas. The particular environment may include one of radiation, steam, dry heat, and plasma sterilization. The indicator may be configured to be substantially the same color as a portion of the medical device before being exposed to the particular environment. The indicator may be configured to be a different color than a portion of the medical device after being exposed to the particular environment. The indicator may be produced directly on a surface of the medical device. The indicator may include a plurality of indicators. Each of the plurality of indicators may undergo a color change different from the other of the plurality of indicators.

In a further embodiment, the invention includes a method of determining a state of a medical device. The method includes providing a medical device having an indicator produced directly on a portion of the medical device, the indicator capable of undergoing a color change when exposed to a particular environment, and viewing the medical device to determine if the indicator has changed color due to exposure to the particular environment.

In various embodiments, the invention may include one, some, or all of the following features. Providing a medical device may include providing a medical device with an indicator printed directly on a portion of the device. Viewing the medical device may include determining if there is a symbol on the device. The particular environment may include a chemical. The chemical may be one of EtO gas and formaldehyde gas. The particular environment may include one of radiation, steam, dry heat, and plasma sterilization. Viewing the medical device may include determining if the indicator is substantially a same color as the portion of the medical device. Viewing the medical device may include determining if the indicator is a different color than the portion of the medical device. The medical device may include a plurality of indicators and viewing the medical device includes determining if any one of the plurality of indicators has changed color. The medical device may include a handle, a distal end effector, and an elongate portion connecting the handle to the distal end effector, and the indicator may be produced directly on the handle.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

The foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate embodiments of the invention and together with the description, serve to explain the principles of the invention.

FIG. 1 is a plan view of an example of a medical device suited for use with a visual indicator according to an embodiment of the present invention.

FIG. 2 is a plan view of a distal end effector of the medical device of FIG. 1.

DESCRIPTION OF THE EMBODIMENTS

Figure 3:
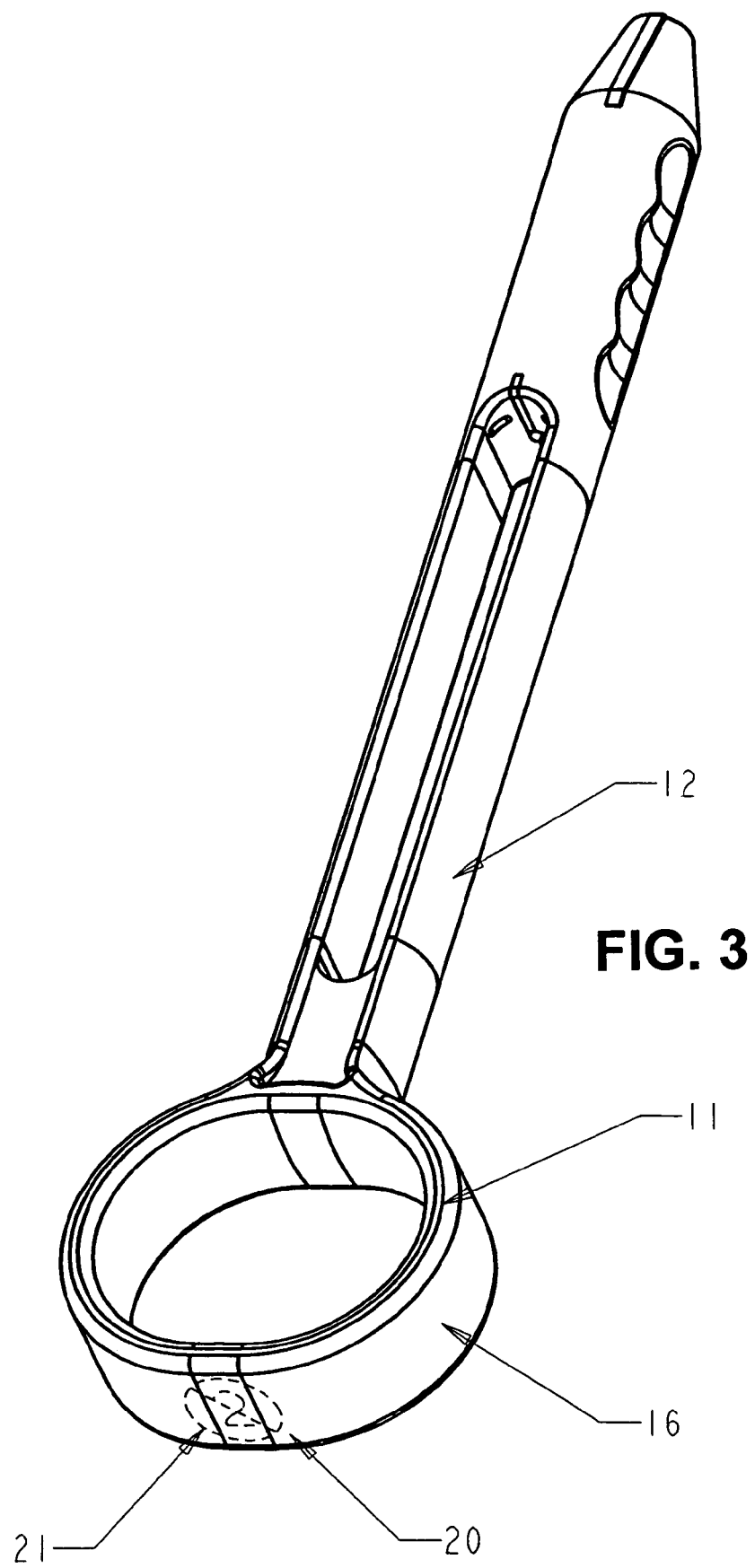
FIG. 3 is a perspective view of an elongate portion and thumb ring of the medical device of FIG. 1, showing a visual indicator in an unexposed state according to an embodiment of the present invention.

Reference will now be made in detail to the present exemplary embodiments of the invention illustrated in the accompanying drawings. Wherever possible, the same reference numbers will be used throughout the drawings to refer to the same or like parts.

Embodiments of the invention relate to a medical device with a visual indicator that indicates to the user the sterility of the medical device and/or whether the medical device has been exposed to potentially hazardous or otherwise undesirable environments and/or chemicals. The visual indicator may be printed on a portion of a medical device, such as the handle, and initially have the same color as that portion. When exposed to a particular environment and/or chemical, the visual indicator changes color so that it has a different color than that portion of the medical device.

FIGS. 1–2 depict an exemplary medical device suitable for use in connection with a visual indicator according to an embodiment of the present invention. The medical device 10 is an endoscopic biopsy forceps device. Device 10 includes a handle having a ring portion 11 connected to the proximal end of an elongate portion 12. A spool portion 13 is disposed around the elongate portion 12 and configured such that the spool portion 13 is longitudinally movable relative to the elongate portion. A flexible, elongate, tubular member 14 is connected at its proximal end to the distal end of the elongate portion 12. At the distal end of the elongate member 14 is a distal end effector assembly 15. Assembly 15 may include any suitable end effector for performing a medical procedure, for example, a pair of biopsy forceps jaws 17. An elongate actuation member, such as a hypotube 18, may extend from spool portion 13 and attach to pull wires 19. These pull wires 19 may extend through member 14, and couple to distal assembly 15. Movement of the spool portion 13 relative to the elongate portion 12 causes the actuation of the distal end effectors, i.e. jaws 17.

The biopsy forceps device 10 shown in FIGS. 1–2 is exemplary of a medical device that may be used in connection with a visual indicator according to embodiments of the invention. Any other endoscopic medical device, including graspers, scissors, snares, etc., or non-endoscopic medical devices, including laparoscopic devices, may be used. In addition, other embodiments of device handles or actuators, end effector assemblies, and connections therebetween may be used with a visual indicator according to embodiments of the invention. The invention is not limited to particular types of medical devices or components of the devices, and instead has broad application to any medical device that would benefit from a visual indication of exposure to an undesirable environment.

Figure 4:
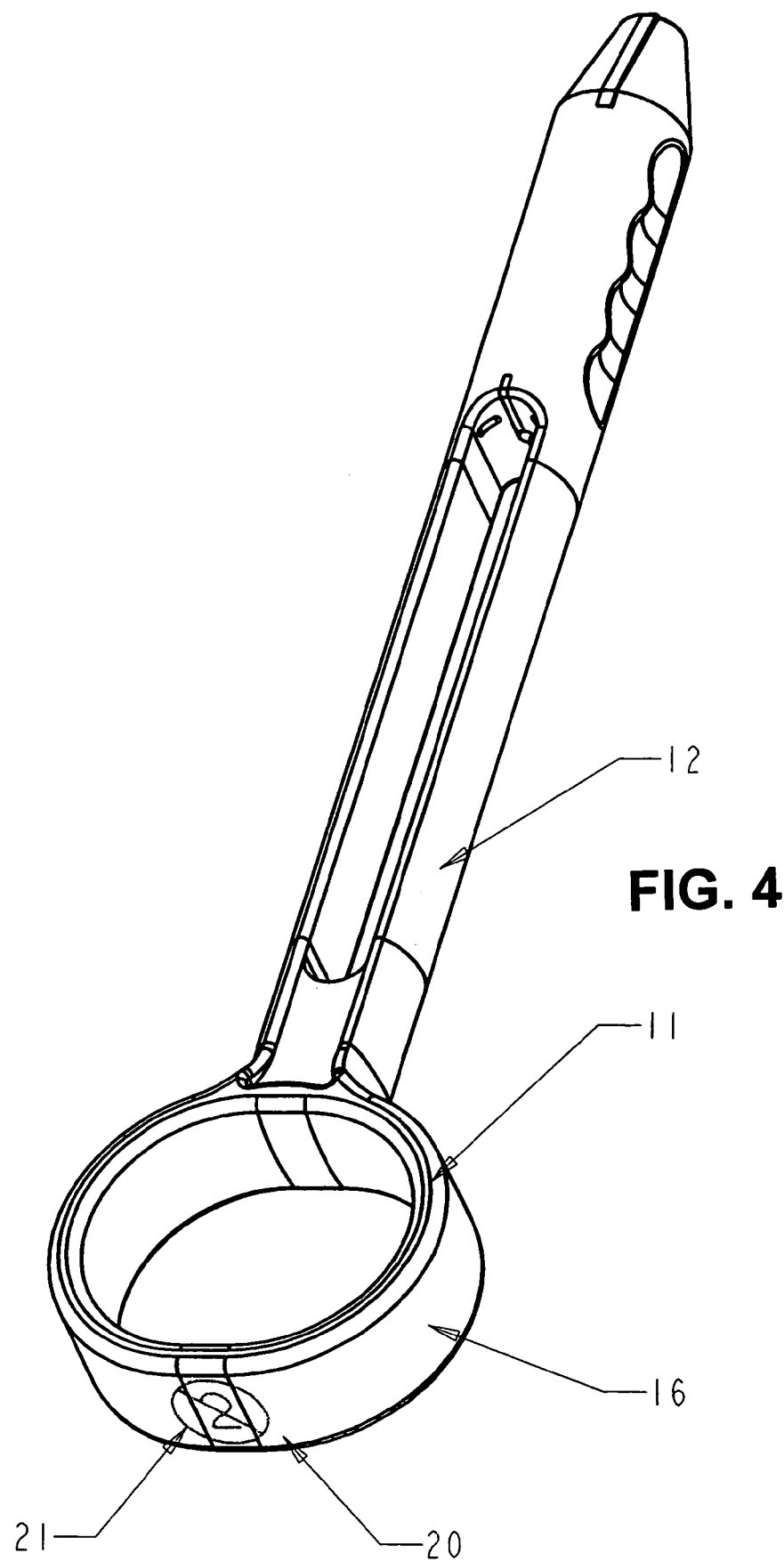
FIG. 4 is a perspective view of the elongate portion and thumb ring of FIG. 3, with the visual indicator in an exposed state.

FIGS. 3–4 show ring portion 11, which has an indicator portion 20 on its outer surface 16 opposite the elongate portion 12. Portion 20 includes an indicator 21. In this particular embodiment, indicator 21 is in the shape of the number two (2) surrounded by a circle with a line through it. This symbol indicates that device 10 is for single use only.

Any other symbol may be used as a visual indicator. Alternatively, the indicator may not be configured as a specific symbol, and instead, for example, may be a shape, such as a circle, or text that can undergo a color change when exposed to certain environments and/or chemicals. Furthermore, the indicator may be of any color initially and may change into any color. The indicator also may include certain ingredients, such as chemicals and/or dyes, that will cause the indicator to undergo any of a plurality of color changes, depending on the environment and/or chemicals that it is exposed to. There may also be a plurality of indicators on various portions of the medical device, each indicator including a different ingredient, such as a chemical and/or dye, that will cause that indicator to change color depending on the environment and/or chemicals it is exposed to. Each such indicator may differ in the environment and/or chemical that causes its color change. In this way, the medical device can indicate whether it has been exposed to any one or more of a variety of undesirable environments or chemicals. In such cases, and for indicators that can undergo a variety of color changes depending on the environment it is exposed to, a color coded chart may be provided with the device so that the user can determine what each color change indicates.

FIG. 3 shows indicator 21 in an unexposed state, i.e. before indicator 21 is exposed to an undesired environment or chemical that would cause indicator 21 to undergo a color change. In this embodiment, indicator 21 is shown as dashed lines because indicator 21 is not visible on the indicator portion 20 (i.e., it is the same color as the indicator portion 20 and/or the rest of the ring portion 11). In this state, indicator 21 and indicator portion 20 have not been exposed to, for example, an unsterilized environment for a prolonged or predetermined period of time, a predetermined temperature, a predetermined humidity, a predetermined amount of radiation, a predetermined chemical or chemicals, or any other undesirable condition that would cause the indicator 21 to change color.

FIG. 4 shows indicator 21 in an exposed state, i.e. after indicator 21 has been exposed to an undesired environment or chemical that would cause indicator 21 to undergo a color change. In this embodiment, indicator 21 is visible on the indicator portion 20 (i.e., it is not the same color as the indicator portion 20 and/or the rest of the ring portion 11) because either the indicator portion 20 has been exposed to, for example, an unsterilized environment for a prolonged or predetermined period of time, a predetermined temperature, a predetermined humidity, a predetermined amount of radiation, a predetermined chemical or chemicals, or any other undesirable condition that would cause the indicator 21 to change color.

In embodiments of the invention, indicator 21 includes an ink that includes various chemicals that cause indicator 21 to transform from the unexposed state to the exposed state. The ink is capable of being printed directly onto the surface of a medical device. As an example, the ink may be based on a flexographic sterilization indicator ink made by Tempil, Inc., #G-FWC-800. The ink may have been reformulated, for example, by adding colorants (e.g., to brighten the white to match the device handle color, for example) and/or solids (e.g., to indicate when the indicator 21 has been exposed to particular gases, such as EtO gas). The ink may already have EtO reactive solids in it, but more may be added. The ink may also have thinners and/or hardeners added to it, for example, so that it is more easily printable on the medical device. The ink may also be formulated so that it does not wash off easily. The indicator 21 may be printed on the indicator portion 20 of the medical device 10 at any point before, during, or after the manufacture of the medical device 10. Any suitable method of printing may be used, including pad printing.

Some examples of flexographic inks made by Tempil, Inc., and their reaction to various environments, include the following, which may be found on the website of Tempil, Inc. at http://www.tempil.com/SterilizationInks.htm:

An originally blue ink that changes to a cocoa-like color when exposed to a dry heat.

An originally blue ink that changes to a cocoa-like color or green when exposed to EtO gas.

An originally blue ink that changes to gray, green, or red when exposed to plasma.

An originally blue, red, white, or yellow ink that changes to a cocoa-like color when exposed to a steam autoclave.

An originally green ink that changes to purple or red when exposed to e-beam radiation.

An originally green ink that changes to purple or red when exposed to gamma radiation.

An originally green ink that changes to purple when exposed to a steam autoclave.

An originally red, white, or yellow ink that changes to a cocoa-like color when exposed to EtO gas.

An originally yellow ink that changes to a cocoa-like color when exposed to formaldehyde gas.

An originally yellow ink that changes to red when exposed to gamma radiation.

The aforementioned colors and their reactions to specific environments are exemplary only, and any combination of the aforementioned colors and/or reactions to specific environments, or any other environment, is also contemplated. In addition, though an embodiment of a visual indicator is described in connection with a specific location on the ring portion 11 of the handle of device 10, a visual indicator and/or the indicator portion may be on any portion of the medical device 10, for example, other portions of the handle.

Figure 5:
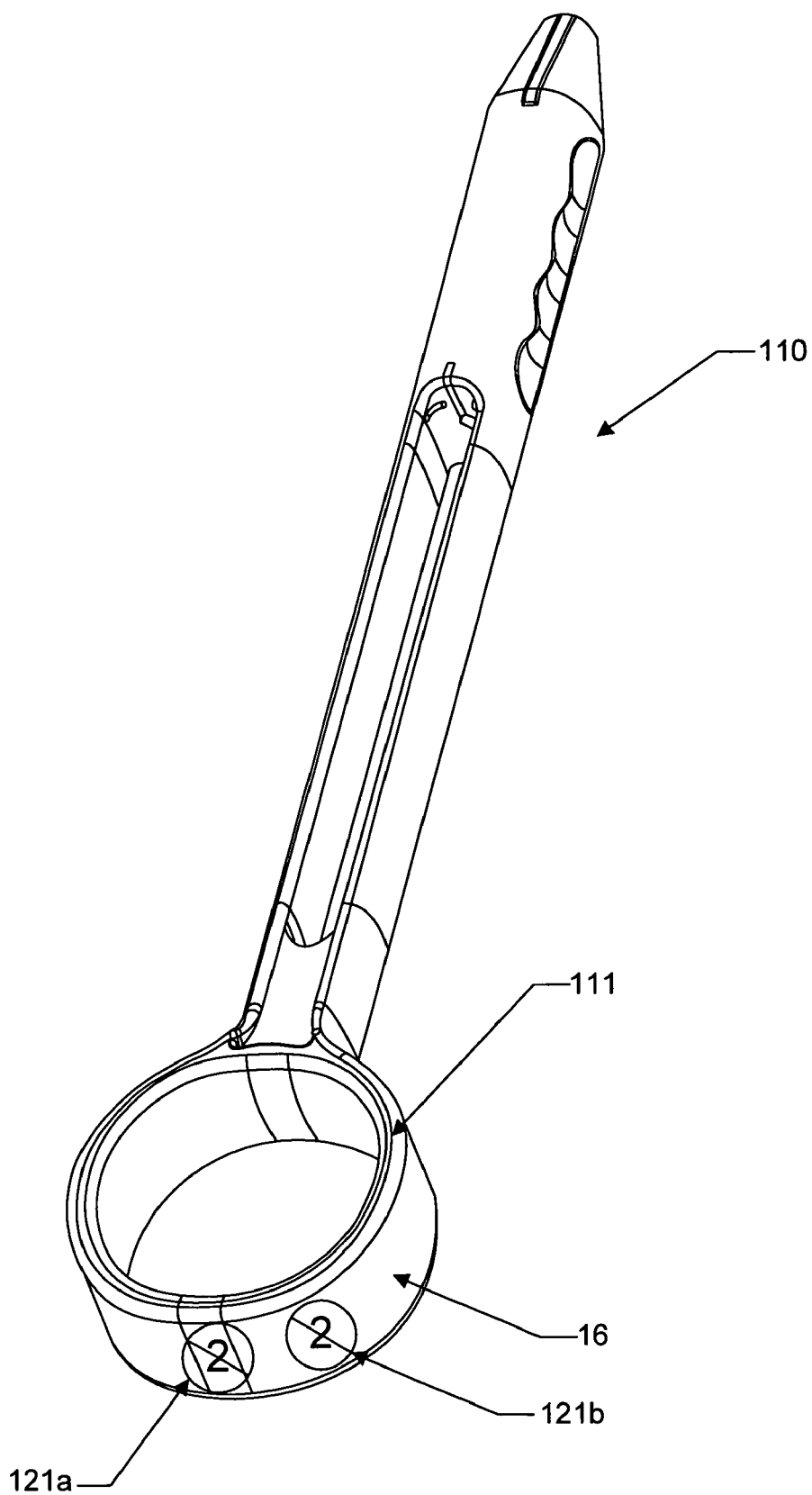
FIG. 5 is a perspective view of an elongate portion and thumb ring including a plurality of indicators according to another embodiment of the invention.

FIG. 5 depicts a device 110 with a ring portion 111 having a plurality of indicators 121a, 121b. Each indicator 121a, 121b may include a different ingredient, such as a chemical and/or dye, that may cause that respective indicator 121a, 121b to change color depending on the environment and/or chemicals it is exposed to. Each such indicator 121a, 121b may differ in the environment and/or chemical that causes its color change. In this way, medical device 110 can indicate whether it has been exposed to any one or more of a variety of undesirable environments or chemicals. In such cases, a color coded chart may be provided with device 110 so that the user can determine what each color change indicates.

Other embodiments of the invention will be apparent to those skilled in the art from consideration of the specification and practice of the invention disclosed herein. It is intended that the specification and examples be considered as exemplary only, with the true scope and spirit of the invention being indicated by the following claims.

What is claimed is:

1. A device to perform a medical procedure comprising:
a medical device; and
an indicator printed directly on the medical device, the indicator including a chemical capable of undergoing a color change when exposed to a particular environment,
wherein the indicator is configured to be substantially the same color as a portion of the medical device before being exposed to the particular environment, and the indicator is configured to change color after a single exposure to the particular environment,
wherein the medical device comprises a handle, a distal end effector, and an elongate portion connecting the handle to the distal end effector,
wherein the indicator is produced directly on the handle.

2. The device of claim 1, wherein the handle comprises a ring portion and an elongate portion.

3. The device of claim 2, wherein the indicator is produced directly on the ring portion.

4. The device of claim 1, wherein the indicator is configured to show a symbol when it undergoes the color change.

5. The device of claim 1, wherein the particular environment includes a chemical.

6. The device of claim 5, wherein the chemical is EtO gas or formaldehyde gas.

7. The device of claim 1, wherein the particular environment includes radiation, steam, dry heat, or plasma sterilization.

8. The device of claim 1, wherein the indicator is configured to be a different color than a portion of the medical device after being exposed to the particular environment.

9. The device of claim 1, wherein the indicator is produced directly on a surface of the medical device.

10. The device of claim 1, wherein the indicator includes a plurality of indicators.

11. The device of claim 10, wherein each of the plurality of indicators undergoes a color change different from the other of the plurality of indicators.

12. The device of claim 1, wherein the indicator is stationary relative to the device during the color change.

13. The device of claim 1, wherein the chemical is configured to change to a first color when exposed to a first environment and change to a second color different from the first color when exposed to a second environment different from the first environment.

14. A medical device comprising:
a handle;
a distal end effector;
an elongate portion connecting the handle to the distal end effector; and
a visual indicator printed directly on a surface of the handle,
wherein the indicator includes a chemical configured to undergo a color change to a different color than the surface of the handle after being exposed to a particular environment, and the indicator is configured to change color after a single exposure to the particular environment.

15. The medical device of claim 14, wherein the indicator is configured to show a symbol when it undergoes the color change.

16. The medical device of claim 14, wherein the particular environment includes a chemical.

17. The medical device of claim 16, wherein the chemical is EtO gas or formaldehyde gas.

18. The medical device of claim 14, wherein the particular environment includes radiation, steam, dry heat, or plasma sterilization.

19. The medical device of claim 14, wherein the indicator includes a plurality of indicators.

20. The medical device of claim 19, wherein each of the plurality of indicators undergoes a color change different from the other of the plurality of indicators.

21. The medical device of claim 14, wherein the indicator is stationary relative to the medical device during the color change.

22. The medical device of claim 14, wherein the chemical is configured to change to a first color when exposed to a first environment and change to a second color different from the first color when exposed to a second environment different from the first environment.

23. A method of determining a state of a medical device, the method comprising:
   providing a medical device having an indicator printed directly on a portion of the medical device, the indicator including a chemical capable of undergoing a color change when exposed to a particular environment, and the indicator is configured to change color after a single exposure to the particular environment; and
   viewing the medical device to determine if the indicator has changed color due to exposure to the particular environment,
   wherein the medical device comprises a handle, a distal end effector, and an elongate portion connecting the handle to the distal end effector, and
   wherein the indicator is produced directly on the handle.

24. The method of claim 23, wherein viewing the medical device includes determining if there is a symbol on the device.

25. The method of claim 23, wherein the particular environment includes a chemical.

26. The method of claim 25, wherein the chemical is EtO gas or formaldehyde gas.

27. The method of claim 23, wherein the particular environment includes radiation, steam, dry heat, or plasma sterilization.

28. The method of claim 23, wherein viewing the medical device includes determining if the indicator is a different color than the portion of the medical device.

29. The method of claim 23, wherein the medical device includes a plurality of indicators and viewing the medical device includes determining if any one of the plurality of indicators has changed color.

30. The method of claim 23, wherein the indicator is stationary relative to the device during the color change.

31. The method of claim 23, wherein the chemical is configured to change to a first color when exposed to a first environment and change to a second color different from the first color when exposed to a second environment different from the first environment.

32. A device to perform a medical procedure comprising:
   a medical device; and
   an indicator printed directly on the medical device, the indicator including a chemical capable of undergoing a color change when exposed to a particular environment,
   wherein the chemical is configured to change to a first color when exposed to a first environment and change to a second color different from the first color when exposed to a second environment different from the first environment,
   wherein the medical device includes a handle, a distal end effector, and an elongate portion connecting the handle to the distal end effector,
   wherein the indicator is produced directly on a surface of the handle.

33. The device of claim 32, wherein the indicator is configured to be a different color than a portion of the medical device after being exposed to the particular environment.

34. The device of claim 32, wherein the indicator is produced directly on a surface of the medical device.

35. The device of claim 32, wherein the indicator includes a plurality of indicators.

36. The device of claim 35, wherein each of the plurality of indicators undergoes a color change different from the other of the plurality of indicators.

37. The device of claim 32, wherein the indicator is stationary relative to the device during the color change.

38. The device of claim 32, wherein the indicator is configured to change color after a single exposure to the particular environment.

39. A device to perform a medical procedure comprising:
   a medical device; and
   a plurality of indicators printed directly on the medical device, each of the plurality of indicators including a chemical capable of undergoing a color change when exposed to a particular environment,
   wherein the medical device includes a handle, a distal end effector, and an elongate portion connecting the handle to the distal end effector,
   wherein each of the plurality of indicators is produced directly on a surface of the handle.

40. The device of claim 39, wherein a first of the plurality of indicators is configured to change color when exposed to a first environment and not change color when exposed to a second environment different from the first environment, and a second of the plurality of indicators is configured to change color when exposed to the second environment and not change color when exposed to the first environment.

41. The device of claim 39, wherein each of the plurality of indicators is configured to be a different color than a portion of the medical device after being exposed to the particular environment.

42. The device of claim 39, wherein each of the plurality of indicators is produced directly on a surface of the medical device.

43. The device of claim 39, wherein each of the plurality of indicators undergoes a color change different from the other of the plurality of indicators.

44. The device of claim 39, wherein each of the plurality of indicators is stationary relative to the device during the color change.

45. The device of claim 39, wherein each of the plurality of indicators is configured to change color after a single exposure to the particular environment.

46. The device of claim 39, wherein the particular environment includes a chemical,
   wherein the chemical is EtO gas or formaldehyde gas.

47. A device to perform a medical procedure comprising:
   a medical device; and
   an indicator printed directly on the medical device, the indicator including a chemical capable of undergoing a color change when exposed to a particular environment, wherein the indicator is configured to be substantially the same color as a portion of the medical device before being exposed to the particular environment, and the indicator is configured to change color after a single exposure to the particular environment, wherein the particular environment includes a chemical, wherein the chemical is EtO gas or formaldehyde gas.

* * * * *